United States Patent [19]

Bernauer et al.

[11] 3,991,197
[45] Nov. 9, 1976

[54] PYRROLIDINES

[75] Inventors: Karl Bernauer, Oberwil; Karlheinz Pfoertner; Fernand Schneider, both of Basel; Hans Schmid, Schwerzenbach, all of Switzerland

[73] Assignee: Hoffmann-La Roche Inc., Nutley, N.J.

[22] Filed: Feb. 12, 1976

[21] Appl. No.: 657,420

[30] Foreign Application Priority Data
Feb. 21, 1975 Switzerland............. 2231/75
Dec. 18, 1975 Switzerland............. 16405/75

[52] U.S. Cl. ............ 424/263; 260/295 AM; 260/296 R
[51] Int. Cl.² ............... C07D 207/02
[58] Field of Search ........... 260/296 R; 424/263

[56] References Cited
OTHER PUBLICATIONS
Bapat, et al., Aust. J. Chem., vol. 21, pp. 2483 to 2520 (1968).
Meyers, J. Org. Chem., vol. 24, pp. 1233 to 1235 (1959).

Primary Examiner—John D. Randolph
Attorney, Agent, or Firm—Samuel L. Welt; Bernard S. Leon; Gerald S. Rosen

[57] ABSTRACT

Compounds represented by the formula

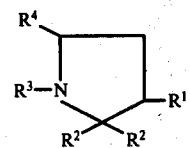

wherein $R^1$ is a pyridyl, $R^2$ is hydrogen or lower alkyl, $R^3$ is hydrogen, lower alkyl or benzyl and $R^4$ is phenyl or phenyl substituted at one or more carbon atoms with one or more of halogen, lower alkyl, lower alkoxy, nitro or amino and pharmaceutically acceptable acid addition salts thereof, having analgesic activity are disclosed.

16 Claims, No Drawings

PYRROLIDINES

DESCRIPTION OF THE INVENTION

The present invention concerns compounds represented by the formula

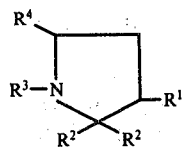

I wherein $R^1$ is a pyridyl, $R^2$ is hydrogen or lower alkyl, $R^3$ is hydrogen, lower alkyl or benzyl and $R^4$ is phenyl or phenyl substituted at one or more carbon stoms with one or more of halogen, lower alkyl, lower alkoxy, nitro or amino, and pharmaceutically acceptable acid addition salts thereof.

As used herein "pyridyl" means 4-pyridyl, 3-pyridyl and 2-pyridyl, with 4-pyridyl being preferred. "Lower alkyl" means straight-chain or branched alkyl groups with 1 to 7 carbon atoms, for example, methyl, ethyl, propyl, butyl, pentyl, hexyl and heptyl, with methyl being preferred. "Halogen" includes fluorine, chlorine, bromine and iodine with chlorine being preferred. "Lower alkoxy" means alkoxy groups with 1-7 carbon atoms, for example, methoxy, ethoxy, propoxy, butoxy and the like with methoxy being preferred.

The compounds within the scope of the formula I have at least two basic nitrogen atoms and can therefore form acid addition salts with inorganic or organic acids, for example, with hydrochloric acid, hydrobromic acid, sulfuric acid, acetic acid, succinic acid, maleic acid, ethanesulfonic acid, p-toluenesulfonic acid and the like. The dihydrochloride salts are the preferred salts.

The salts of the compounds within the scope of formula I can also be in the form of a hydrate, for example, mono, tri- or polyhydrate.

Preferred compounds within the scope of formula I are those wherein $R^1$ is a 4-pyridyl, particularly those wherein $R^2$ is methyl.

The compounds within the scope of formula I can be a mixture of cis- and trans-isomers. The isomers can, if desired, be separated into the individual isomers, for example, by means of fractional crystallization. The cis-isomers are especially preferred.

The less preferred isomers can, if desired, be isomerized either prior to or after the separation of the isomers. This isomerization can be accomplished by dehydrogenation and subsequent hydrogenation. The dehydrogenation can be effected, for example, by N-halogenation, especially N-chlorination, e.g., with an alkali metal hypochlorite, and subsequent cleavage of hydrogen halide by means of a base, e.g., with sodium methylate. The thus obtained pyrroline can then be reduced to the desired isomer.

The compounds within the scope of formula occur as a racemate which can be resolved into the optical antipodes, by conventional means, for example, using optically active acids such as dibenzoyltartaric acid, camphorsulfonic acid and the like. The laevorotatory antipodes (3R,5S) are the especially preferred antipode.

The compounds within the scope of formula I possess a pharmacodynamic action and can accordingly be used as active substances in pharmaceutical preparations. The active compounds of this invention can be formulated into pharmaceutical preparations which contain a pharmaceutically acceptable organic or inorganic inert carrier material suitable for enteral or parenteral application, such as e.g., water, gelatin, lactose, starch, magnesium stearate, talc, vegetable oils, gum, polyalkylene glycols, Vaseline and the like. The The pharmaceutical preparations can be in solid form, e.g., as tablets, dragees, suppositories, capsules or in liquid form, e.g., solutions, suspensions or emulsions. Such preparations can be sterilized and can contain pharmaceutically acceptable adjuvants such as preservatives, stabilizers, wetting agents, emulsifiers, salts for varying the osmotic pressure or buffers. The preparations can also contain other therapeutically valuable substances.

The compounds within the scope of formula I have an analgesic action without being addictive. They can thus be used for the control of pain. Thus, for example, rac-4-(cis-2,2-dimethyl-5-phenyl-3-pyrrolidinyl)-pyridine dihydrochloride has an $ED_{50}$ of 47 (30 minutes) or 79 (60 minutes) mg/kg in the writhing test with oral administration to the mouse. The toxicity of this substance in the mouse amounts to 103 mg./kg. and in the rat to 212 mg./kg. (5 day toxicity). In the hotplate test the compound has an $ED_{50}$ of 96 (30 minutes) or 76 (60 minutes). As used herein the $ED_{50}$ is that dose at which the compound is active in 50% of the mice.

The compounds within the scope of formula I can be administered as analgesically active substances to humans in single doses of about 50–200 mg. 1–3 times daily. Oral administration is preferred.

The compounds of this invention can be manufactured by reducing a compound represented by the formula

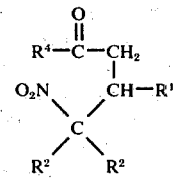

II wherein $R^1$, $R^2$ and $R^4$ are the same as in formula I and any amino group present on the phenyl at $R^4$ is protected or a compound represented by the formula

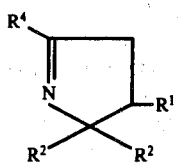

III or an N-oxide thereof, wherein $R^1$, $R^2$ and $R^4$ are the same as in formula II, and cleaving off the protecting group of any protected amino group present. If desired, a lower alkyl or a benzyl as defined in formula I can be introduced into the resulting compound which is that of formula I wherein R³ is hydrogen. Also if desired, a phenyl group can be nitrated and a base of formula I can be converted into an acid addition salt. Also if desired any mixture of cis- and trans-isomers obtained can be separated and the undesired isomer can be isomerized. Any racemate thus obtained can be cleaved into its optical antipodes.

The compounds of this invention within the scope of formula I are produced by cyclizing compounds represented by formula II under reducing conditions. The reduction can be carried out catalytically, by means of noble metal catalysts, for example, by means of platinum, or by means of Raney nickel catalyst under elevated pressure, for example, under a pressure of more than 2 atmospheres. In carrying out the reduction with the foregoing reducing agents, the resulting products are predominantly in the cis configuration.

The cyclizing reduction of the starting materials can, however, also be effected by means of a nascent hydrogen, manufactured by the action of acids on metals. The hydrogen can be produced in this case, for example, by the action of glacial acetic acid on zinc, especially zinc dust, or on iron, especially iron powder. The reduction with zinc or iron and acid can be carried out at temperatures between about 0° C. and about 80° C., preferably at about 60° C. With this type of reduction, the products which result are predominantly in the trans-configuration.

The reductive cyclization of the starting materials, however, also can be effected by means of tin and glacial acetic acid, preferably at the boiling temperature of the reaction mixture, leading to compounds of formula III or to their corresponding N-oxides. The resulting compounds can be converted into the compounds of formula I in a second step according to the reduction methods given above, i.e., catalytically or with zinc or iron and glacial acetic acid or with complex hydrides such as sodium borohydride, lithium aluminum hydride or the like.

The compounds of formula I obtained in the manner described from the compounds of formula II or formula III or the N-oxides of the latter, are unsubstituted at the nitrogen, i.e, R³ is hydrogen. If desired, a lower alkyl or benzyl can be introduced onto these compounds. Methyl can be introduced, for example, by methylating a compound of formula I, wherein R³ is hydrogen, in a conventional manner by means of formaldehyde and formic acid. Higher akyles and benzyl can be introduced by first acylating such compounds within the scope of formula I, for example, with the appropriate acid halide or acid anhydride and reducing the acyl compound obtained in this manner, for example, with lithium aluminum hydride. Thus, for example, a compound of formula I, wherein R³ is benzyl, can be obtained by acylating the appropriate compound within formula I wherein R³ is hydrogen by means of benzoyl chloride and reducing the thus obtained benzoyl compound with lithium aluminum hydride.

If a protected amino is present in the phenyl at R⁴, e.g., an acylamino such as acetylamino, it is converted into the free amino by treatment with a base, for example, with ethanolic potassium hydroxide.

A compound of formula III wherein R⁴ is a nitro-substituted phenyl can be converted into the corresponding amino substituted phenyl of formula I by reduction of the nitro group.

A nitro can be introduced onto a phenyl at R⁴ of a compound of formula I. The reaction is effected by nitration with a suitable nitrating agent such as nitric acid, preferably the nitration is effected with a mixture of concentrated nitric acid and concentrated sulfuric acid with cooling.

Acid addition salts of the base compounds of formula I can be obtained by treatment of these compounds with the appropriate acids.

Preferred compounds of this invention are those from starting materials wherein the two R² substituents are methyl.

Also preferred are starting materials wherein R⁴ is phenyl or phenyl substituted by chlorine or methoxy. More especially preferred are the compounds of formula I, wherein R¹ is a 4-pyridyl, the two R² substituents are methyl. R³ is hydrogen and R⁴ is chlorine or methoxy substituted, preferably phenyl or p-methoxyphenyl, as well as their acid addition salts, especially the dihydrochlorides.

The starting materials of formula II belong to a known group of compounds.

The starting materials of formula III as well as their acid addition salts and their N-oxides can be obtained by cyclizing a compound of the formula

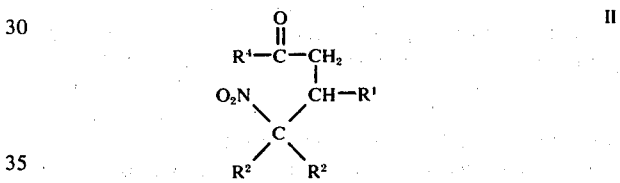

wherein if an amino is present in the phenyl at R⁴ it is a protected amino, R¹ and R² are the same as in formula I, under reducing conditions and cleaving off the protecting group of any protected amino present, or by irradiating an azirine of the formula

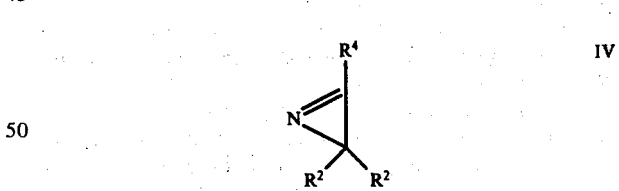

wherein R² and R⁴ are the same as in formula I, together with a vinylpyridine of the formula

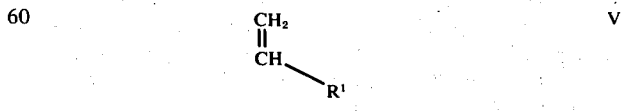

wherein R¹ is the same as in formula I, with ultraviolet light. The resulting compounds of formula III can be converted in acid addition salt or an N-oxide, and resulting racemates can be resolved into its optical antipodes.

The reductive cyclization of the compounds of formula II can be effected by means of tin and glacial acetic acid, preferably at the boiling temperature of the reaction mixture. In this case there is obtained, depending on the reaction conditions, a compound of formula III or its N-oxide.

The reductive cyclization of the compounds of formula II to compounds of formula III can also be effected under specific reaction conditions by means of zinc and glacial acetic acid. Thus, in order to prevent further reduction of the compounds of formula I, it is necessary to use a small amount of zinc and short reaction times The starting material used in the photochemical reaction process for the producing compounds of formula III, i.e., the azirines of formula IV as well as the vinylpyridines of formula V belong to known groups of compounds.

The ultraviolet irradiation of a mixture of compounds of formulas IV and V is expediently effected in a inert organic solvent, for example, in benzene, dioxane, hexane, methylene chloride or the like. Room temperature or a somewhat higher temperature is expediently employed for counter. however, temperatures higher than 40° C. should be avoided.

The irradiation is preferably effected under an inert gas atmosphere, for example, nitrogen or argon, with carbond dioxide excluded from the atmosphere.

The ultraviolet light source used preferably radiates light of a wavelength between about 300 nm. and about 365 nm. The use of ultraviolet light with a wavelength between about 300 and about 330 nm. is especially preferred.

Light suitable for this irradiation can be produced, for example, with a 2000 watt mercury high-pressure lamp, which is provided with a copper sulfate filter (35 g. of copper sulfate per 1 liter of water; thickness of layer, 1 cm) or with a Pyrex glass filter The base compounds of formula III can be converted into acid addition salts or into N-oxides by conventional means. The N-oxides can be produced, for example, by treatment of the compounds of formula III with peracids or hydrogen peroxide.

The following examples illustrate the invention.

EXAMPLE 1

Three times in intervals of 30 minutes, 20 g. of zinc dust are added each time with stirring to a solution of 22.3 of 4-methyl-4-nitro-3-(4-pyridyl)-valerophenone in 900 ml. of glacial acetic acid. The resulting mixture is left under stirring for a further hour, filtered, the residue which forms is washed with water. The filtrate is evaporated under reduced pressure. The residue is treated with aqueous potassium carbonate and extracted with methylene chloride. The extract is dried over sodium sulfate and evaporated under reduced pressure. The product is crystallized with ethyl acetate and isopropyl ether, then treated with 110 ml. of 1 n HCl. The resulting mixture is evaporated under reduced pressure and the residue crystallized from ethanol/acetone. The resulting product, trans-4-(2,2-dimethyl-5-phenyl-3-pyrrolidinyl)-pyridine dihydrochloride is obtained in the form of crystals which decompose at 240° C.

EXAMPLE 2

A solution of 34 g. of 3',4',5'-trimethoxy-4-methyl-4-nitro-3-(4-pyridyl)-valerophenone in 340 ml. of glacial acetic acid is heated at 50°–60° C. with stirring. There are added portionwise 34 g. of zinc dust. The resulting mixture is left to react for 1 hour. Then a further 34 g. of zinc dust are added and after another hour, the reaction mixture is filtered. The filter residue is washed with glacial acetic acid and the filtrate evaporated under reduced pressure. The residue is taken up in water, make alkaline with potassium carbonate and extracted three times with ethyl acetate. The organic phase is washed with water, dried over sodium sulfate and evaporated under reduced pressure. The residue which results is crystallized with ether to obtain trans-4-[2,2-dimethyl-5-(3,4,5-trimethoxyphenyl)-3-pyrrolidinyl]-pyridine with a melting point of 117°–119° C. The corresponding oxalate, recrystallized from methanol, has a melting point of 228°–230° C. (decomp.).

EXAMPLE 3

44 G. of 3',4',5'-trimethoxyacetophenone and 440 ml. of water are heated at 70° C. with stirring and treated with 20.2 ml. of isonicotinaldehyde. Then, there are added, three times at intervals of 30 minutes, 4 ml. each time of a 6% sodium hydroxide solution in water/methaol (2:1). The resulting reaction mixture is kept overnight at 70° C., cooled in an ice-bath and the resulting crystals are filtered off then washed with ethanol and ether to result in a product with a melting point at 124°–127° C. After recrystallization from methanol/ether there are obtained crystals of melting ppont 128°–130° C. The mother liquors are evaporated under reduced pressure, taken up in ethyl acetic and the organic phase is washed twice with water. The washings are extracted twice with ethyl acetate and the combined organic phases dried over sodium sulfate and evaporated under reduced pressure. The residue is chromatographed on a 30-fold amount of silica gel (ether/diethylamine 95:5) and after recrystallization from ethanol/ether, there are obtained 3',4',5'-trimethoxy-3-(4-pyridyl)-acrylophenone of melting point 127°–129° C.

EXAMPLE 4

A solution of 40 g. of 3',4',5'-trimethoxy-3-(4-pyridyl)-acrylophenone and 24 g. of 2-nitropropane in 270 ml. of ethanol is heated at reflux with stirring under a nitrogen atmosphere. Within 1 hour there is added dropwise a sodium ethylate solution (manufactured from 1.35 g. of sodium and 27 ml. of ethanol). The reaction mixture left standing for a half hour to react further is then evaporated under reduced pressure. The residue results is taken up in methylene chloride, washed with water, dried over sodium sulfate and evaporated under reduced pressure. The product which results is crystallized with chloroform ether to yield 3',4',5'-trimethoxy-4-methyl-4-nitro-3-(4-pyridyl)-valerophenone, melting point 214°–216° C.

EXAMPLE 5

18 G. of zinc dust are added portionwise with stirring to a solution of 18 g. of 4-methyl-4,4'-dinitro-3-phenyl-valerophenone in 500 ml. of glacial acetic acid. The reaction mixture is stirred for a further 1 hour and an additional 18 g. of zinc dust are added. The reaction mixture is then left to stand overnight then filtered. The filter residue which results is washed with glacial acetic acid and the filtrate evaporated is under reduced pressure. The residue is treated with ethyl acetate and the organic phase washed several times with dilute ammonia, dried over sodium sulfate and evaporated under reduced pressure. The residue is treated with 70 ml. of acetic anhydride and 35 ml. of pyridine and left to stand for 1 hour at room temperature. The resulting precipitated crystals are filtered off and washed with ethyl acetate to yield 4'-[5,5-dimethyl-4-(4-pyridyl)-1-pyrrolin-2-yl]-acetanilide with a melting point of 222°–225° C.

Through heating this compound is ethanolic KOH under reflux one obtains 4-[2-(p-aminophenyl)-5,5-dimethyl-1-pyrrolin-4-yl]-pyridine which can be reduced to the corresponding 4-[5-(p-aminophenyl)-2,2-dimethyl-3-pyrrolidinyl]-pyridine.

EXAMPLE 6

41.25 G. of 4'-nitroacetophenone are suspended in 500 ml. of water and heated at 70° C. with stirring. Then, 24 ml. of isonicotinaldehyde are added and the reaction mixture is treated three times at intervals of 30 minutes with 5 ml. each time of a 6% NaOH solution in water/methanol (2:1). Subsequently the reaction mixture is left to react at 70° C. for 8 hours. The crystals which form are filtered off, boiled up twice with 500 ml. of ethanol each time and subsequently washed with ether to yield 4'-nitro-3-(4-pyridyl)-acrylphenone with a melting point of 218°–221° C.

EXAMPLE 7

22.5 G. of 2-nitropropane and 49.1 g. (0.193 mol) of 4'-nitro-3-(4-pyridyl)-acrylophenone are taken up in 2 l. of dioxane and 5 ml. of water and heated to 80° C. with stirring. 5 Ml. of Triton B* (40% in methanol) are added and the reaction mixture is left to react for 8 hours, with addition of 5 ml. of Triton B per hour for a total 40 ml. of Triton B. Then reaction mixture is evaporated under reduced pressure. The residue which results is treated with ethyl acetate/methanol and left to crystallize. After several recrystallizations, 34.3 g. of 4-methyl-4,4'-dinitro-3-phenylvalerophone with a melting point of 161°–164° C. is obtained.

*Triton B is an emulsifying agent from Rohm and Haas, Philadelphia, Pa.

EXAMPLE 8

A solution of 44.7 g. of 4-methyl-4-nitro-3-(3-pyridyl)-valerophenone in 420 ml. of glacial acetic acid is heated at 60° C. with stirring and treated portionwise with 44.7 g. of zinc dust. After 1 hour, an additional 44.7 g. of zinc dust are added and the reaction mixture is left to react for an additional hour. The cooled reaction mixture is filtered, the filter residue washed with glacial beingnabled acetic acid and the filtrate evaporated under reduced pressure. The residue is taken up in 400 ml. of water and made alkaline with potassium carbonate. The reaction mixture is extracted three times with 200 ml. of ethyl acetate each time, the organic phase is washed twice with water, dried over sodium sulfate and evaporated under reduced pressure. The resulting residue is crystallized with isopropyl ether and there is obtained a product with a melting point of 60°–61° C. The mother liquors are chromatographed on a 50-fold amount of silica gel with ether/diethylamine (95.5) and, after crystallization with isopropyl ether, there is obtained trans-3-(2,2-dimethyl-5-phenyl-3-pyrrolidinyl)-pyridine, with a melting point of 57°–58° C. A methanolic solution of the base product is treated with a methanolic solution of oxalic acid to obtain pH 6. The obtained crystals are washed with ether and the oxalate of the product with a melting point of 224°–225° C. is obtained.

EXAMPLE 9

147 G. of 96% sulfuric acid are added to a solution of 53.6 g. of pyridin-3-aldehyde and 60 g. of acetophenone in 1000 ml. of glacial acetic acid and the reaction mixture is left to stand at room temperature for 100 hours. The reaction mixture then is poured into 3 liters of water, made alkaline with potassium carbonate and extracted three times with ethyl acetate. The organic phase is washed three times with water, dried over sodium sulfate and evaporated under reduced pressure. The resulting residue is crystallized from methanol. The product obtained has a melting point of 99°–100° C. The mother liquors are chromatographed on a 30-fold amount of silica gel with ether/diethylamine (95:5), 1-phenyl-3-(3'-pyridyl)-2-propen-1-one [3-(3-pyridyl)-acrylophenone], the product which is obtained therefrom by crystallization from methanol has a melting point of 98°–99° C.

EXAMPLE 10

A solution of 51.8 g. of 3-(3-pyridyl)-acrylophenone and 44.2 g. of 2-nitropropane in 496 ml. of ethanol are heated at reflux with stirring in a nitrogen atmosphere. Then, a sodium ethylate solution manufactured from 2.54 g. of sodium and 49.6 ml. of ethanol is added dropwise within 1 hour. The reaction mixture is left standing for an additional half hour to react further and then evaporated under reduced pressure. The resulting residue is taken up in 1000 ml. of methylene chloride, washed three times with 300 ml. of water each time, dried over sodium sulfate, evaporated under reduced pressure and crystallized from methanol to yield 4-methyl-4-nitro-3-(3-pyridyl)-valerophenone with a melting point of 134°–135° C.

EXAMPLE 11

14 G. of 3-(p-chlorophenyl)-2,2-dimethyl-2H-azirine and 14.2 g. of freshly distilled 2-vinylpyridine in 2 l. of benzene are irradiated for 11 hours in an inert atmosphere (nitrogen or argon) at room temperature with ultraviolet light from a 2000 watt mercury high-pressure lamp using a copper sulfate filter (35 g. of CuSO$_4$.6H$_2$O in 1 liter of water) of 1 cm layer thickness. Then, the solvent is evaporated under reduced pressure and the oily residue chromatographed with cyclohexane/acetone (85:15) on silica gel. The combined fractions are freed from solvent under reduced pressure. The residue is taken up in n-pentane. At 4' C. 2-[2-(p-chlorophenyl)-5,5-dimethyl-1-pyrrolin-4-yl]-pyridine with a melting point of 85° C. crystallizes.

EXAMPLE 12

9.5 G. of 2-[2-(p-chlorophenyl)-5,5-dimethyl-1-pyrrolin-4-yl]-pyridine are dissolved in 50 ml. of absolute ethanol and treated with 1.5 g. of sodium borohydride. The reaction mixture is stirred under an inert atmosphere (nitrogen) at room temperature overnight and then a further 0.35 g. of sodium borohydride are added. After an additional 4 hours, the reaction mixture is evaporated to dryness under reduced pressure, taken up in water and extracted with methylene chloride.

After evaporation of the solvent from the organic phase an oil remains which is dissolved in ethanolic hydrochloric acid. After the addition of ether, 2-[cis-5-(p-chlorophenyl)-2,2-dimethyl-3-pyrrolidinyl]-pyridine dihydrochloride of melting point 204° C. crystallizes out.

EXAMPLE 13

30 G. of 3-(m-methoxyphenyl)-2,2-dimethyl-2H-azirine and 24 g. of freshly distilled 4-vinylpyridine are irradiated in 2 l. of absolute benzene for 11 hours under the conditions given in Example 11. Thereafter, the reaction mixture is evaporated to dryness under reduced pressure and taken up in ether. The fractions insoluble in ether are filtered off and the ethereal solution treated with diisopropyl ether. At +4° C. 4-[2-(m-methoxyphenyl)-5,5-dimethyl-1-pyrrolin-4-yl]-pyridine of melting point 112°–113° C. crystallizes out overnight.

EXAMPLE 14

17 G. of 4-[2-(m-methoxyphenyl)-5,5-dimethyl-1-pyrrolin-4-yl]-pyridine are dissolved in 250 ml. of absolute ethanol and stirred in an inert gas atmosphere together with 8 g. of sodium borohydride for 24 hours at room temperature. After evaporation of the solvent, the resulting residue is taken up in water and thoroughly extracted with ether. The ether phase is dried with magnesium sulfate and evaporated under reduced pressure. The resulting residue is dissolved in ethanolic hydrochlorid acid from which 4-[cis-5-(m-methoxyphenyl)-2,2-dimethyl-3-pyrrolidinyl]-pyridine dihydrochloride of melting point 233° C. (decomp.) crystallizes overnight.

EXAMPLE 15

20 G. of 4-[2-(m-methoxyphenyl)-5,5-dimethyl-1-pyrrolin-4-]-pyridine, dissolved in 200 ml. of formic acid and 100 ml. of water, are treated with stirring at −5° C. to 0° C. ten times, each with 8 g. of zinc dust at intervals of a half hour. The reaction mixture is stirred for a total of 10 hours. The zinc sediment is then filtered off. The reaction mixture is concentrated under reduced pressure and made strongly alkaline (pH 12) with sodium hydroxide. Ether extraction produces a pyrrolidine compound with a cis/trans ratio of 1:4. This compound is dissolved in methanol and treated with 25 ml. of concentrated hydrochloric acid. The reaction mixture is evaporated to dryness under reduced pressure and taken up in 60 ml. of methanol at the boiling point. From the thus obtained solution there crystallizes on cooling a product with a cis/trans ratio of 1:10. Recrystallization from methanol yields 97% trans-compound, i.e., 4-[trans-5-(5m-methoxyphenyl)-2,2-dimethyl-3-pyrrolidinyl]-pyridine dihydrochloride with a melting point of 204°–205° C.

EXAMPLE 16

12 G. of 2,2-dimethyl-3-phenyl-2H-azirine and 15 g. of freshly distilled 4-vinylpyridine are irradiated in 2 l. of absolute benzene for 6½ hours under the conditions given in Example 11. The brown oil remaining after evaporation is chromatographed on silica gel, firstly with benzene, then with an increasing acetone content (up to a ratio of benzene/acetone 1:1). The combined fractions are evaporated under reduced pressure. The residue is recrystallized twice from n-hexane and the resulting yellow solutions are decolorized with active carbon to yield 4-(5,5-dimethyl-2-phenyl-1-pyrrolin-4-yl)-pyridine with a melting point of 90°–92° C.

EXAMPLE 17

55 G. of 4-(5,5-dimethyl-2-phenyl-1-pyrrolin-4-yl)-pyridine are dissolved in 1 l. of absolute ethanol and treated in an inert gas atmosphere while stirring at room temperature with 20 g. of sodium borohydride. After 3 hours, an additional 20 g. of sodium borohydride are added and the reaction mixture is stirred overnight. The solvent is then evaporated under reduced pressure and the residue taken up in water. The resulting mixture is then thoroughly extracted with chloroform. The chloroform phase is then dried with magnesium sulfate and evaporated to dryness under reduced pressure. The residue which results is taken up in 200 ml. of diisopropyl ether. At −18° C. 4-(cis-2,2-dimethyl-5-phenyl-3-pyrrolidinyl)-pyridine of melting point 75°–76° C. crystallizes out.

46 G. of the thus obtained product are dissolved in methanol and treated with sufficient ethanolic hydrochloric acid to result in a clearly acidic reaction. After the addition of diethyl ether 4-(cis-2,2-dimethyl-5-phenyl-3-pyrrolidinyl)pyridine dihydrochloride with a melting point of 244° C. crystallizes out.

EXAMPLE 18

0.6 G. of zinc dust are added under agitation, twice at intervals of 90 minutes to a solution of 0.6 g. of 4-methyl-4-nitro-3-(4-pyridyl)-valerophenone in 25 ml. of acetic acid. The reaction mixture is allowed to stand for another hour then it is filtered and the filtrate dried under reduced pressure. The residue which results is mixed with aqueous ammonia and extracted with ethyl acetate. The organic phase is washed with water, then twice with a solution of sodium acetate in acetic acid at pH 5 and once again with water. Following the last water wash, the pH is adjusted with ammonia to pH 8 and the organic phase is extracted once more with ethyl acetate.

The combined organic extracts are dried over sodium sulfate and evaporated under reduced pressure. The residue is crystallized twice from isopropyl ether to yield 4-(5,5-dimethyl-2-phenyl-1-pyrrolin-4-yl)-pyridine with a melting point of 98°–99° C.

EXAMPLE 19

28 G. of 3-(p-chlorophenyl)-2,2-dimethyl-2H-azirine and 28 g. of freshly distilled 4-vinylpyridine are irradiated in 4 l. of absolute benzene for 13 hours under the conditions given in Example 11. The unreacted 4-vinylpyridine is distilled off from the brown oil remaining after evaporation at 41° C. and 0.01 Torr. The residue is taken up in hot n-hexane and the solution decolorized with active carbon. 4-[2-(p-chlorophenyl)-5,5-dimethyl-1-pyrrolin-4-yl]-pyridine with a melting point of 97°–98° C. crystallizes at room temperature.

EXAMPLE 20

18 G. of 4-[2-(p-chlorophenyl)-5,5-dimethyl-1-pyrrolin-4-yl]-pyridine are dissolved in 300 ml. of absolute ethanol and stirred together with 20 g. of sodium borohydride under an inert gas atmosphere for 24 hours at room temperature. Then the solvent is evaporated under reduced pressure and the residue taken up in water. The reaction mixture is then thoroughly extracted with chloroform and the separated chloroform phase is dried with magnesium sulfate. After evaporation of the chloroform under reduced pressure, the residue is dissolved in 60 ml. of methanol and treated with ethanolic hydrochloric acid until the reaction is clearly acidic. After the addition of diethyl ether 4-[cis-5-(p-chlorophenyl)-2,2-dimethyl-3-pyrrolidinyl]-pyridine hydrochloride with a melting point of 229° C. crystallizes out.

EXAMPLE 21

15 G. of 3-(p-methoxyphenyl)-2,2-dimethyl-2H-azirine and 18 g. of freshly distilled 4-vinylpyridine are irradiated in 2 l. of absolute benzene for 8 hours under the conditions given in Example 11. The brown oil remaining after evaporation of the solvent is taken up in a small amount of warm acetone. At +4° C. 4-[2-(p-methoxyphenyl)-5,5-dimethyl-1-pyrrolin-4-yl]-pyridine with a melting point of 131° C. crystallizes out.

EXAMPLE 22

18 G. of 4-[2-(p-methoxyphenyl)-5,5-dimethyl-1-pyrrolin-4-yl]-pyridine are dissolved in 300 ml. of absolute ethanol and stirred together with 24 g. of sodium borohydride in an inert gas atmosphere at room temperature for 24 hours. After evaporation of the solvent under reduced pressure, the residue is taken up in water and thoroughly extracted with chloroform. The separated chloroform phase is dried with magnesium sulfate and re-evaporated under reduced pressure. The remaining oil is dissolved in a small amount of ethanol and treated with ethanolic hydrochloric acid until the reaction is clearly acidic. After the addition of diethyl ether 4-[cis-5-(p-methoxyphenyl)-2,2-dimethyl-3-pyrrolidinyl]-pyridine hydrochloride of melting point 215° C. crystallizes out.

EXAMPLE 23

16 G. of 3-(p-methylphenyl)-2,2-dimethyl-2H-azirine and 26 g. of freshly distilled 4-vinylpyridine are irradiated in 2 l. of absolute benzene for 6 hours under the conditions given in Example 11 with the addition of 0.05 g. of p-hydroquinone. After evaporation of the solution under reduced pressure there remains a brown oil from which the excess 4-vinylpyridine is distilled off at 41°–42° C. and 0.01 Torr. The residue is taken up in a small amount of acetone. The crude crystallizate obtained from the acetone solution is chromatographed withe benzene/acetone (95:5) on silica gel. The combined fractions are evaporated to dryness under reduced pressure. Then, the residue is recrystallized twice with n-hexane, the solution which results is then decolorized with active carbon to yield 4-[2-(p-methylphenyl)-5,5-dimethyl-1-pyrrolin-4-yl]-pyridine with a melting point of 102° C.

EXAMPLE 24

24 G. of 4-[2-(p-methylphenyl)-5,5-dimethyl-1-pyrrolin-4-yl]-pyridine are dissolved in 750 ml. of absolute ethanol and stirred in an inert gas atmosphere together with 24 g. of sodium borohydride at room temperature for 24 hours. Then, the solvent is evaporated under reduced pressure and the residue taken up in water. The resulting mixture is then thoroughly extracted with ether. The separated ether phase is dried with magnesium sulfate and the ether evaporated under reduced pressure. The residue which results is dissolved in ethanol and treated with ethanolic hydrochloric acid. After the addition of ether 4-[cis-5-(p-methylphenyl)-2,2-dimethyl-3-pyrrolidinyl]-pyridine hydrochloride (melting point 242°–243° C.) crystallizes out.

EXAMPLE 25

15 g. of 3-(o-chlorophenyl)-2,2-dimethyl-2H-azirine and 20 g. of freshly distilled 4-vinylpyridine are irradiated in 2.1 of absolute benzene for 5 hours under the conditions given in Example 11. Thereafter, the reaction solution is concentrated under reduced pressure and excess 4-vinylpyridine distilled off at 1.3 mmHg. and 37°–60° C. The oily residue which results is chromatographed with cyclohexane/acetone (7:3) on silica gel. The crude product obtained from the combined fractions is dissolved in n-pentane/acetone. At −18° C. 4-[2-(o-chlorophenyl)-5,5-dimethyl-1-pyrrolin-4-yl]-pyridine of melting point 60°–61° C. crystallizes out.

EXAMPLE 26

8 G. of 4-[2-(o-chlorophenyl)-5,5-dimethyl-1-pyrrolin-4-yl]-pyridine are dissolved in 200 ml. of absolute ethanol and stirred overnight in an inert gas atmosphere together with 4 g. of sodium borohydride at room temperature. The solvent is then evaporated under reduced pressure. The residue which results is taken up in water and thoroughly extracted with ether. The ether phase is then dried with magnesium sulfate and evaporated to dryness under reduced pressure. The residue which results is then dissolved in ethanolic hydrochloric acid. After treating with ether, rac. 4-[cis-5-(o-chlorophenyl)-2,2-dimethyl-3-pyrrolidinyl]-pyridine dihydrochloride of melting point 208°–210° C. (decomp.) crystallizes out during 30 hours.

EXAMPLE 27

15 G. of 3-(m-chlorophenyl)-2,2-dimethyl-2H-azirine and 20 g. of freshly distilled 4-vinylpyridine are irradiated in 2 l. of absolute benzene for 4 hours under the conditions given in Example 11. After concentration of the reaction solution under reduced pressure, the excess 4-vinylpyridine is distilled off at 1 mmHg and 37° C. and the oily resiude is chromatographed with cyclohexane/acetone (7:3) on silica gel. The crude product obtained from the combined fractions after evaporation of the solvent is crystallized at +4° C. from a mixture of 200 ml. of petroleum ether (fraction 80°–105° C.) and 20 ml. of diisopropyl ether to yield 4-[2-(m-chlorophenyl)-5,5-diemethyl-1-pyrrolin-yl]-pyridine (melting point 97° C.).

EXAMPLE 28

11 G. of 4-[2-(m-chlorophenyl)-5,5-dimethyl-1-pyrrolin-4-yl]-pyridine are dissolved in 200 ml. of absolute ethanol and stirred at room temperature in an inert gas atmosphere together with 6 g. of sodium borohydride for 24 hours. After evaporation of the solvent under reduced pressure, the residue which results is taken up in water and thoroughly extracted with ether. The ether phase is dried with magnesium sulfate and evaporated to dryness under reduced pressure. The residue which results is then dissolved in ethanolic hydrochloric acid from which 4-[cis-5-(m-chlorophenyl)-2,2-dimethyl-3-pyrrolidinyl]-pyridine dihydrochloride of melting point 232°–238° C. (decomp.) crystallizes out overnight.

EXAMPLE 29

15 G. of 2,2-diethyl-3-phenyl-2H-azirine and 15 g. of freshly distilled 4-vinylpyridine are irradiated in 2 l. of absolute benzene for 4.25 hours under the conditions given in Example 11. After evaporation of the solvent under reduced pressure, the resulting oily residue is distilled at 0.3 mmHg and 165° C. to yield 4-(5,5-diethyl-2-phenyl-1-pyrrolin-4-yl)-pyridine in the form of a light-yellow oil.

EXAMPLE 30

15.5 G. of 4-(5,5-diethyl-2-phenyl-1-pyrrolin-4-yl)-pyridine are dissolved in 350 ml. of absolute ethanol and stirred at room temperature in an inert gas atmosphere together with 10 g. of sodium borohydride for 48 hours. After evaporation of the solvent, the resulting residue is taken up in water and thoroughly extracted with ether. The other phase is dried with magnesium sulfate and evaporated to dryness under reduced pressure. The resulting residue is dissolved in ethanolic hydrochloric acid from which 4-(cis-2,2-diethyl-5-phenyl-3-pyrrolidinyl)-pyridine dihydrochloride of melting point 238°-242° C. (decomp.) crystallizes out overnight.

EXAMPLE 31

12 G. of 4-(cis-2,2-dimethyl-5-phenyl-3-pyrrolidinyl)-pyridine are introduced into 20 ml. of formic acid while cooling. Then, 9 ml. of a 35% formaldehyde solution are added thereto and the reaction mixture is boiled at reflux for 1 hour. After the addition of 10 ml. of concentrated hydrochloric acid, formic acid and excess formaldehyde are distilled off under reduced pressure. The resulting solid residue is crystallized from ethanol/ether to yield 4-(cis-1,2,2-trimethyl-5-phenyl-3-pyrrolidinyl)-pyridine dihydrochloride (melting point 246°C.).

EXAMPLE 32

13.5 Ml. of benzoyl chloride are allowed to drop into a solution of 22.8 g. of 4-(cis-2,2-dimethyl-5-phenyl-3-pyrrolidinyl)-pyridine in 180 ml. of pyridine while stirring in the course of 1 hour. Then, the resulting deep-red solution is poured into ice-cold water and extracted with ether. The ether phase is washed several times with water and dried with magnesium sulfate. The residue obtained after evaporation of the ether is dissolved in a small amount of acetone. After the addition of a small amount of diisopropyl ether the N-benzoyl compound crystallizes. 1.8 G. of lithium aluminum hydride are suspended in 200 ml. of absolute ether and 12.4 g. of the N-benzoyl compound is introduced into this suspension in small portions within 3 hours while stirring under nitrogen. Subsequently, the reaction mixture is heated at reflux for an additional 6 hours. Then, the reaction mixture is layered by the slow addition of ice-water and the ether phase is dried and evaporated. The residue which results is taken up in alcoholic hydrochloric acid and treated with ether from which 4-(cis-1-benzyl-2,2-dimethyl-5-phenyl-3-pyrrolidinyl)-pyridine dihydrochloride (melting point 164°-166° C.) crystallizes. EXAMPLE 33

Zinc dust is added in increments of 5 g. eight times while stirring at −5° C. to 0° C. at intervals of a half hour to a solution of 20 g. of 4-[2-(p-methoxyphenyl)-5,5-dimethyl-1-pyrrolin-4-yl]-pyridine in 200 ml. of formic acid and 100 ml. of water. After 13 hours the resulting zinc sediment is separated and the formic acid substantially distilled off under reduced pressure. Then, the resulting residue is adjusted to pH 7 with aqueous sodium carbonate. 2G. of starting material are recovered by ether extraction of the sodium carbonate solution. The reaction mixture is then made alkaline (pH 13–14) with sodium hydroxide solution and re-extracted with ether. The pyrrolidine obtained after evaporation of this ether phase is a cis/trans mixture in the ratio 1:4 which is taken up in methanol and treated with 10 ml. of concentrated hydrochloric acid. After the addition of acetone thereto a product crystallizes initially with cis/trans ratio 1:4, then from the mother liquors at a ratio of cis/trans 1:10. The latter product is recrystallized from methanol to yield a product which consist of 98% of the trans-form, i.e., 4-[trans-5-(p-methoxyphenyl)-2,2-dimethyl-3-pyrrolidinyl]-pyridine dihydrochloride (melting point 227°-229° C.).

EXAMPLE 34

9.5 G. of 2,2-dimethyl-3-phenyl-2H-azirine and 12 g. of freshly distilled 2-vinylpyridine are irradiated in 2 l. of benzene for 7 hours under the conditions given in Example 11. After evaporation of the solvent under reduced pressure, the resulting residue is taken up in 400 ml. of n-pentane and decolorized with active carbon. After 48 hours at −18° C., the crude product which crystallizes is recrystallized from n-pentane/small amount of benzene to yield 2-(5,5-dimethyl-2-phenyl-1-pyrrolin-4-yl)-pyridine (melting point 101°-102° C.).

EXAMPLE 35

9.5 G. of 2-(5,5-dimethyl-2-phenyl-1-pyrrolin-4-yl)-pyridine dissolved in 50 ml. of absolute ethanol is treated with 1.5 g. of sodium borohydride and stirred overnight under nitrogen at room temperature. Then, a further 0.5 g. of sodium borohydride is added and the reaction mixture is stirred for an additional 4 hours. Subsequently, the mixture is evaporated to dryness under reduced pressure. The resulting residue is taken up in water and extracted with methylene chloride. After evaporation of the previously dried organic phase under reduced pressure, a yellow oil remains. The oil is dissolved in ethanolic hydrochloric acid. After the addition of ether to the ethanolic hydrochloric acid solution 8.3 g. of 2-(cis-2,2-dimethyl-5-phenyl-3-pyrrolidinyl)-pyridine dihydrochloride (melting point 232°-235° C.) crystallizes therefrom overnight.

EXAMPLE 36

30 Ml. of sodium hypochlorite ($Cl_2 = 10\%$) are added to a solution of 5.1 g. of 4-[trans-2,2-dimethyl-5-(3,4,5-trimethoxyphenyl)-3-pyrrolidinyl]-pyridine in 50 ml. of $CH_2Cl_2$. While stirring, the reaction mixture is heated at 50° C. for 2 hours. 10 Ml. of sodium hypochlorite are added and the reaction mixture is left to react for 2 more hours. After a further addition of 10 ml. of sodium hypochlorite and an additional 2 hours, the reaction mixture is treated with water and extracted three times with methylene chloride. The organic phase which results is washed with water, dried over sodium sulfate and evaporated under reduced pressure to yield crude 4-[trans-1-chloro-2,2-dimethyl-5-(3,4,5-trimethoxyphenyl)-3-pyrrolidinyl]-pyridine.

EXAMPLE 37

A solution of 7.5 g. of 4-(5,5-dimethyl-2-(3,4,5-trimethoxyphenyl)-1-pyrrolin-4-yl)-pyridine in 75 ml. of methanol is treated with 1.6 g. of sodium borohydride while stirring. After 2 hours, an additional 1.6 g. of sodium borohydride is added and the reaction mixture is left to react for another 2 hours. Then the reaction mixture is evaporated under reduced pressure and the residue is taken up in water and extracted three times with ethyl acetate. The resulting organic phase is washed with water, dried over sodium sulfate and evaporated under reduced pressure. The residue is filtered through a 10-fold amount of silica gel and eluted with benzene/ether/petroleum ether (low boiling)/CH$_2$Cl$_2$./methanol/ethyl acetate (1:1:1:1:2:2). Crystallization with ethyl acetate/isopropyl ether, yields 4 g. of 4-[cis-2,2-dimethyl-5-trimethoxyphenyl)-3-pyrrolidinyl]-pyridine, melting point 96°–97° C. The oxalate, recrystallized from methanol/ether, has a melting point of 210°–212° C.

EXAMPLE 38

9.8 G. of 4-[trans-1-chloro-2,2-dimethyl-5-(3,4,5-trimethoxyphenyl)-3-pyrrolidinyl]-pyridine are treated with 52 ml. of sodium methylate solution (10 g. of sodium per 100 ml. of methanol) and heated at 50° C. for 3 hours. Then the reaction mixture is treated with water and extracted three times with ethyl acetate. The organic phase is washed with water, dried over sodium sulfate and evaporated under reduced pressure. The residue is crystallized with ethyl acetate/isopropyl ether to yield 4-(5,5-dimethyl-2-(3,4,5-trimethoxyphenyl)-1-pyrrolin-4-yl)-pyridine, melting point 143°–144° C. This compound is, as in Example 37, reduced with sodium borohydride to the cis-pyrrolidinyl compound. This example shows therefore the isomerization of trans/pyrrolidines by way of a pyrroline to the corresponding cis-pyrrolidine.

EXAMPLE 39

18 G. of zinc powder are added to a solution of 18.0 g. of 4-methyl-4,4'-dinitro-3-(4-pyridyl)-valerophenone in 500 ml. of glacial acetic acid while stirring. After one hour, an additional 18 g. of zinc powder are added and the reaction mixture is left to react overnight. Then the reaction mixture is filtered, the filter residue is washed with dilute acetic acid and the filtrate evaporated under reduced pressure. The resulting residue is treated with dilute ammonia solution and extracted with ethyl acetate. The extract is dried over sodium sulfate and evaporated under reduced pressure to obtain a residue, which is then treated with a mixture of 70 ml. of acetic anhydride and 35 ml. of pyridine. After 1 hour, the crystals which precipitate are filtered off and washed with ethyl acetate to yield 4'-[5,5-dimethyl-4-(4-pyridyl)-1-pyrrolin-2-yl]-acetanilide, which is recrystallized from methanol to give a product with a melting point of 227°–228° C.

EXAMPLE 40

5.8 G. of 4'-[5,5-dimethyl-4-(4-pyridyl)-1-pyrrolin-2-yl]-acetanilide are treated with a solution of 5.8 g. of potassium hydroxide in 58 ml. of ethanol and heated under reflux for 5 hours. Then the reaction mixture is evaporated under reduced pressure and the residue is treated with water. The resulting crystals are filtered and washed well with water. The mineral is dried and recrystallized from methanol/ether to yield 4-[2-(p-aminophenyl)-5,5-dimethyl-1-pyrrolin-4-yl]-pyridine of melting point 175°–178° C. The hydrochloride, recrystallized from methanol/ether, has a melting point of 290°–300° C.

EXAMPLE 41

0.55 G. of sodium borohydride are added to a solution of 1.85 g. of 4-[2-(p-aminophenyl)-5,5-dimethyl-1-pyrrolin-4-yl]-pyridine in 18.5 ml. of methanol and the mixture is stirred at room temperature for 2 hours. Then, an additional 0.55 g. of sodium borohydride are added and the reaction mixture is left to stand at room temperature overnight. The reaction mixture is then evaporated under reduced pressure and the resulting residue taken up in water and extracted three times with methylene chloride. The organic phase is dried over sodium sulfate and evaporated under reduced pressure. The resulting crude product is chromatographed on silica gel with chloroform/methanol/ethyl acetate/ammonia (60:10:2:1). The material obtained, after crystallization with ether, yields 4-[cis-5-(p-aminophenyl)-2,2-dimethyl-3-pyrrolidinyl]-pyridine of melting point 119°–120° C. The trihydrochloride, recrystallized from methanol/ether, has a melting point of 223°–226° C.

EXAMPLE 42

A solution of 3.1 g. of 4'-[5,5-dimethyl-4-(4-pyridyl)-1-pyrrolin-2-yl]-acetanilide in 100 ml. of glacial acetic acid is heated to 50° C. while stirring. 3.1 G. of zinc powder are added thereto and the reaction mixture is left to react for 1 hour. Then an additional 3.1 g. of zinc powder are added and the reaction mixture is left at this temperature for an additional hour. The reaction mixture is left to cool to room temperature and then filtered. The filter residue is washed with water and the filtrate is evaporated under reduced pressure. The resulting residue is treated with water. The resulting mixture is made alkaline with ammonia and extracted three times with ethyl acetate. The organic phase is washed twice with water, dried over sodium sulfate and evaporated. The residue is treated with ethereal hydrochloric acid and recrystallized from ethanol/acetone to yield trans-4'-[5,5-dimethyl-4-(4-pyridyl)-2-pyrrolidinyl]-acetanilide hydrochloride, melting point 248°–249° C. (decomp.).

EXAMPLE 43

0.18 G. of 4'-[trans-5,5-dimethyl-4-(4-pyridyl)-2-pyrrolidinyl]-acetanilide are treated with a solution of 0.18 g. of potassium hydroxide in 1.8 ml. of ethanol and boiled under reflux for 48 hours. The resulting reaction mixture is then evaporated under reduced pressure and the residue is treated with water and extracted three times with methylene chloride. The organic phase is dried over sodium sulfate and evaporated under reduced pressure. The residue which results is treated with ethereal HCl and crystallized with ethanol/ether to yield 4-[trans-5-(p-aminophenyl)-2,2-dimethyl-3-pyrrolidinyl]-pyridine trihydrochloride of melting point 240°–242° C.

EXAMPLE 44

2.83 G. of 4-[cis-5-(p-methoxyphenyl)-2,2-dimethyl-3-pyrrolidinyl]-pyridine (racemate) and 2.50 g. of (+)-camphor-10 β-sulfonic acid monohydrate are boiled at reflux in a mixture of 80 ml. of benzene and 10 ml. of acetone. The boiling mixture is treated dropwise with methanol until all solid constituents have gone into solution. Upon cooling to room temperature the salt with the laevorotatory base crystallizes in colorless long needles. The reaction is filtered and the filter is washed with benzene. The crystallizate is then decomposed with sodium hydroxide solution and the free base separated by shaking out with ether. The ether phase is dried with magnesium sulfate, evaporated under reduced pressure and the remaining oil freed from residual solvent in a high vacuum at room temperature. Optical rotation of the base $[\alpha]_D = -64.7°$ in chloroform. Subsequently, the oil is taken up in ethanolic hydrochloric acid. From this solution after the addition of some ether, 4-[(3R,5S)-5-(p-methoxyphenyl)-2,2-dimethyl-3-pyrrolidinyl]-pyridine dihydrochloride of melting point 236° C. crystallizes.

EXAMPLE 45

7 G. of 4-(cis-2,2-dimethyl-5-phenyl-3-pyrrolidinyl)-pyridine (racemate) and 7 g. of (+)-camphor -10 β-sulfonic acid monohydrate are dissolved in 70 ml. of freshly distilled acetonitrile at boiling. The reaction mixture is left to stand at room temperature for 16 hours and white needles are obtained from which the base is liberated with sodium hydroxide solution. The reaction mixture is shaken out several times with ether, the ether phase is dried with magnesium sulfate and the solvent evaporated. There remain a colorless oil with an optical rotation $[\alpha]_D = -72.7°$ (CHCl$_3$). The oil is dissolved in 30 ml. of boiling n-hexane. After 12 hours at room temperature colorless crystals form with an optical rotation $[\alpha]_D = 74.0°$ hydrochloric acid and treated with ether to yield crystals of 4-[(3R,5S)-2,2-dimethyl-5-phenyl-3-pyrrolidinyl]-pyridine dihydrochloride of melting point 244° C.

EXAMPLE 46

34.5 G. of (−) tartaric acid are added to a solution of 57.5 g. of rac.-4-(5,5-dimethyl-2-phenyl-1-pyrrolin-4-yl)-pyridine in 920 ml. of ethyl acetate and the reaction mixture is boiled under reflux for 30 minutes. The mixture is then cooled, crystallized at ice-bath temperature and filtered. The resulting crystals are washed with a small amount of cold ethyl acetate, dried and dissolved in 500 ml. of water. Then, a saturated aqueous sodium bicarbonate solution is added until a pH 8 is reached and the liberated base is left to crystallize out. The crystals are filtered off and washed with water. Subsequently, the crystals are dissolved in methylene chloride. The resulting organic phase is dried over sodium sulfate and evaporated under reduced pressure to obtain a crystalline substance of $[\alpha]_D = -66°$, $c = 4$ (CHCl$_3$). The mother liquors are treated with 325 ml. of glacial acetic acid and 13 ml. of conc. sulfuric acid and heated under reflux overnight. The reaction mxiture is evaporated under reduced pressure, the residue treated with water and made alkaline with potassium carbonate. The mixture is then extracted three times with ethyl acetate, dried over sodium sulfate and evaporated under reduced pressure. The residue having $[\alpha]_D = 0°$, $c = 5$ (CHCl$_3$) is dissolved in 500 ml. of ethyl acetate and 19 g. of (−)-tartaric acid are added. The resulting mixture is heated under reflux for 30 minutes and then cooled in an ice-bath and left to crystallize out. The crystals are filtered and the dissolved in water, adjusted to pH 8 with a saturated sodium bicarbonate solution and left to crystallize out again. The resulting crystals are filtered and taken up in methylene chloride. The resulting organic phase is dried over sodium sulfate and evaporated under reduced pressure to obtain a crystalline material of $[\alpha]_D = -67°$; $c = 8$ (CHCl$_3$). The crystals having $[\alpha]_D = -66°$ and 10 g., $[\alpha]_D = -67°$ are combined and treated with ether. The resulting precipitated crystals which are filtered off have $[\alpha]_D = -20°$, $c = 2$ (CHCl$_3$). These crystals and the mother liquors are evaporated to yield crystals of $[\alpha]_D = -90°$, $c = 5$ (CHCl$_3$). These crystals are treated with ether again and the resulting precipitated crystals which are filtered off have $[\alpha]_D = -40°$, $c = 5$ (CHCl$_3$). The evaporated mother liquors produce crystals of $[\alpha]_D = -101°$ C., $c = 7$ (CHCl$_3$). Three further crystallizations of the mother liquor produce pure 4-[4R(5,5-dimethyl-2-phenyl-1-pyrrolin-4-yl)]-pyridine, $[\alpha]_D = -151°$, $c = 7$ (CHCl$_3$), melting point 60°–63° C.

EXAMPLE 47

1.25 G. of 4-[(4R)-5,5-dimethyl-2-phenyl-1-pyrrolin-4-yl]-pyridine are dissolved in 12.5 ml. methanol. 0.38 G. sodium borohydride are added and the reaction mixture is allowed to stand for two hours at room temperature. Thereafter, another 0.38 g. sodium borohydride are added and the reaction mixture is allowed to stand for an additional two hours at room temperature. The resulting reaction mixture is dried under reduced pressure. Water is added to the residue and the resulting mixture is extracted three times with methylene chloride. The organic phase is dried over sodium sulfate and evaporated under reduced pressure. The residue is crystallized from n-hexane and filtered to obtain crystals of $[\alpha]_{589} = -26°$ (CHCl$_3$, $c = 3$) and mother liquor of $[\alpha]_D = -74°$ (CHCl$_3$, $c = 7$). The mother liquor is crystallized with hexane to yield crystals of $[\alpha]_{589} = -78°$ (CHCl$_3$, $c = 3$, melting point 78–80°C.). The product obtained is 4-[(3R,5S)-2,2-dimethyl-5-phenyl-3-pyrrolidinyl]-pyridine.

EXAMPLE 48

104 G. of 4-[(4R)-2-(p-methoxyphenyl)-5,5-dimethyl-1-pyrrolin-4-yl]-pyridine are dissolved in 1040 ml. of methanol. 35 G. of platinum oxide are added to the mixture which is hydrogenated. The hydrogenation is accomplished by absorbing the theoretical amount of hydrogen. The catalyst is then filtered off from the reaction mixture which is then washed with warm methanol and dried under reduced pressure. The residue is treated with ethereal hydrochloric acid and crystallized from methanol ether. The crystals are filtered and dried under reduced pressure to yield a hydrochloride salt of melting point 209°–211° C. The salt is dissolved in water, treated with calcium carbonate and extracted with methylene chloride. After drying the extract and evaporating, the product 4-[(3R,5S)-2,2-dimethyl-5-(p-methoxyphenyl)-3-pyrrolidinyl]-pyridine with $[\alpha]_D = -65.8°$ (CHCl$_3$, $c = 1$) is obtained.

EXAMPLE 49

148 G. of racemic 4-[2-(p-methoxyphenyl)-5,5-dimethyl-1-pyrrolin-4-yl]-pyridine were dissolved in 280 ml. acetonitrile and 450 ml. ethylacetate. 150 G. of (+)-camphersulfonic acid are added and the reaction mixture is heated on a steam bath until all reactants are in solution. The resulting solution is cooled on an ice bath until crystallization begins, then it is allowed to crystallize at room temperature for 2.5 hours. The crystals are filtered and washed with ethyl acetate. The crystals are taken up in water and calcium carbonate is added until a pH 9 is reached and recrystallization occurs. The crystals are filtered, washed with water and taken up in methylene chloride. The organic phase which results is dried over sodium sulfate and evaporated under reduced pressure to obtain crystals of 4-[(4R)-2-(p-methoxyphenyl)-5,5-dimethyl-1-pyrrolin-4-yl]-pyridine: $[\alpha]_D = -152°$ (CHCl$_3$, $c = 5$).

The mother liquor from the above separation is dried under reduced pressure. The residue is treated with water and alkaline calcium carbonate. Crystallization occurs and the crystals are filtered, washed with water and dissolved in methylene chloride. The resulting organic phase is dried over sodium sulfate and evaporated under reduced pressure. The resulting crystals are heated overnight in a nitrogen atmosphere under reflux in 1190 ml. of 6% ethanolic potash. The reaction mixture is then evaporated under reduced pressure. The resulting residue is treated with 1 liter of water and allowed to crystallize. The crystals are filtered, washed with water, and dissolved in 1 liter methylenechloride. Then the solution is dried over sodium sulfate and evaporated under reduced pressure to yield a racemate: $[\alpha]_D = 0°$ (CHCl$_3$, $c = 4$). The racemate can be separated into its components.

EXAMPLE 50

27.8 G. of 4-[(R)-5,5-dimethyl-2-(2,4-xylyl)-1-pyrrolin-4-yl]-pyridine are dissolved in 278 ml. methanol. 10 G. active carbon and 10 g. platinum oxide are added thereto and the mixture is hydrogenated. After the necessary amount of hydrogen is taken up, the reaction mixture is filtered and washed good with hot methanol. The filtrate then is evaporated under reduced pressure. The substance obtained is treated with ethereal hydrochloric acid. The crystals which form are filtered, washed with ether and crystallized from methanol-ether to obtain the hydrochloride, melting point 210°–214° C. The hydrochloride is dissolved in water, alkaline calcium carbonate is put in the solution which is then extracted with methylene chloride. The resulting organic phase is tried over sodium sulfate and evaporated under reduced pressure to obtain amorphous 4-[3R, 5S]-2,2-dimethyl-5-(2,4-xylyl)-3-pyrrolidinyl-pyridine, $[\alpha]_D = -77.8°$ (CHCl$_3$, $c = 1$).

EXAMPLE 51

16.7 G. racemic 4-[5,5-dimethyl-2-(2,4-xylyl)-1-pyrrolin-4-yl]-pyridine and 9 g. (—)-tartaric acid are dissolved in 167 ml. methanol under reflux. The reaction mixture is allowed to cool to room temperature and after two hours crystallization occurred the crystals are filtered with suction and dissolved in water. The solution is made alkaline with sodium bicarbonate and extracted three times, each time with 100 ml. methylenechloride. The organic phase which results is dried over sodium sulfate and evaporated under reduced pressure to obtain a substance with a rotation of $[\alpha]_D = 127°$ (CHCl$_3$, $c = 4$).

The substance obtained and 2.6 g. (—)-tartaric acid are dissolved in 48 ml. ethanol under reflux. The reaction mixture is allowed to cool to room temperature and within two hours crystallization occurs. The crystals are filtered and dissolved in water. The solution is made alkaline with sodium bicarbonate and extracted three times, each time with 25 ml. methylenechloride. The resulting organic phase is dried over sodium sulfate and evaporated under reduced pressure to obtain 4-[(R)-5,5-dimethyl-2-(2,4-xylyl)-1-pyrrolin-4-yl]-pyridine with $[\alpha]_D = -172°$ (CHCl$_3$, $c = 7$), melting point 50°–51° C. The hydrochloride is made with ethereal hydrochloric acid. It has a melting point of 235°–239° C. (methanolether) and $[\alpha]_D = -156°$ (H$_2$O, $c = 1$).

The mother liquor of the enantiomer obtained above is dissolved in water, made alkaline with sodium bicarbonate and extracted three times with methylenechloride. The resulting organic phase is dried over sodium sulfate and evaporated under reduced pressure to obtain a substance which is heated overnight under reflux in 140 ml. glacial acetic acid and 5 ml. concentrated sulfuric acid. The reaction mixture is then evaporated under reduced pressure and the residue mixed with water and made alkaline with potassium carbonate. The reaction mixture is extracted three times, each time with 150 ml. methylenechloride, dried over sodium sulfate and evaporated under reduced pressure to obtain the racemate with $[\alpha]_D = 0°$ (CHCl$_3$, $c = 8$). This racemate can be separated into its components.

EXAMPLE 52

20 G. of 4-(cis-2,2-dimethyl-5-phenyl-3-pyrrolidinyl)-pyridine (racemate) are dissolved under cool temperatures (5°–10° C.) in concentrated nitric acid and 50 ml. of cool concentrated sulfuric acid are slowly added. Thereafter, the reaction mixture is stirred for about 1 hour at 10°–15° C. and then poured on ice. The pH of the reaction mixture is then adjusted to pH 8–9 with 3N sodium hydroxide, also in the cold, and exhaustively extracted with methylenechloride. The combined extracts are dried over sodium sulfate and evaporated in a water pump vacuum to dryness. The product thereby obtained is a mixture of pyrrolidine with para and meta nitrophenyl substituents. The mixture is dissolved in 400 ml. warm ethanol. After the addition of 25 ml. concentrated hydrochloric acid and some ether, a mixture of dihydrochlorides (m-nitrophenyl and p-nitrophenyl, 8 to 2) is obtained. Fractional crystallization from ethanol yields 4-[cis-2,2-dimethyl-5-(m-nitrophenyl)-3-pyrrolidinyl]-pyridine dihydrochloride (racemate) with a melting point of 229°–232° C. (decomp.).

The mother liquor of the first crystallization is dried in a water pump vacuum to dryness and taken up in 2-propanol. After addition of ether, crystallization occurred to yield 4-[cis-2,2-dimethyl-5-(p-nitrophenyl)-3-pyrrolidinyl]-pyridine dihydrochloride (racemate) with a melting point of 195°–205° C. (decomp.).

EXAMPLE 53

36 G. of 4-[cis-2,2-dimethyl-5-(4-methoxyphenyl)-3-pyrrolidinyl]-pyridine (racemate) is dissolved in the cold (5°–10° C.) in 60 ml. concentrated nitric acid and 60 ml. of cool concentrated sulfuric acid are slowly added. The reaction mixture is stirred about 1 hour at 10°–15° C. and then poured on ice. The pH of the reaction mixture is made 8–9 with 3N sodium hydroxide, also cool, and then extracted exhaustively with ether. The combined extracts are dried over sodium sulfate and evaporated in a water pump vacuum to dryness. The residue is taken up in warm methanol. The addition of 45 ml. concentrated hydrochloric acid and a small amount ether results in crystals of 4-[cis-5-(4-methoxy-3-nitrophenyl)-2,2-dimethyl-3-pyrrolidinyl]-pyridine dihydrochloride which after recrystallization from methanol has a melting point of 233° C.

EXAMPLE 54

140.2 G. of 4-[2-(p-methoxyphenyl)-5,5-dimethyl-1-pyrrolin-4-yl]-pyridine is dissolved in 1.5 l. methanol and hydrogenated with a platinum oxide catalyst in methanol. After 9750 ml. hydrogen is absorbed, 30 ml.

glacial acetic acid is added to the reaction mixture. After an additional 1.3 l. hydrogen are absorbed the reaction mixture is added to fresh 30 glacial acetic acid, filtered, and dried at 50° C. (100 Torr.). The residue is dissolved in water and agitated with ether five times, each time with 100 ml. ether. The ether phase is rejected. The aqueous solution is made alkaline by adding 250 ml. concentrated ammonia and then mixed three times, each time with 250 ml. methylenechloride. The combined methylene chloride phase is washed with 500 ml. water and then mixed with 340 ml. 3N hydrochloric acid. The aqueous phase is mixed with 300 ml. methylene chloride and then brought to crystallization by drying under reduced pressure yielding a crystal/liquid mixture. 100 Ml. water are added thereto and the solution is heated, then mixed with 350 ml. of acetone until it starts to become turbid. The mixture then is put in a refrigerator overnight. The reaction mixture is filtered and washed with an ice-cold acetone-water (2:1) mixture. The resulting crystals are renewed by dissolving in 150 ml. of hot water and crystallized after addition of 350 ml. acetone in the refrigerator. Filtering and drying 5 hours at 60° C./12 Torr. yields 150 g. of 4-[5-(p-methoxyphenyl)-2,2-dimethyl-3-pyrrolidinyl]-pyridine dihydrochloride trihydrate.

EXAMPLE 55

Tablets

| Ingredients | Amounts |
| --- | --- |
| 4-(2,2-dimethyl-5-phenyl-3-pyrrolidinyl)-pyridine dihydrochloride | 130.0 mg. |
| Mannitol | 100.0 mg. |
| Maize starch | 145.0 mg. |
| Polyvinylpyrrolidone | 15.0 mg. |
| Talc | 9.0 mg. |
| Magnesium stearate | 1.0 mg. |
| | 400.0 mg. |

The active substance is mixed with the mannitol and a portion of the maize starch and sieved.

The resulting powder mixture is dissolved in a suitable solvent with the polyvinylpyrrolidone, granulated in the usual manner and dried.

Then, the remaining ingredients are admixed and the is pressed to tablets of appropriate size.

EXAMPLE 56

An injection solution is manufactured as follows: 129 g. of 4-(2,2-dimethyl-5-phenyl-3-pyrrolidinyl)-pyridine dihydrochloride are dissolved in liter of water for injection purposes. The solution is filtered fiber-free under nitrogen gassing and filled into 1 cm³-ampules, likewise under nitrogen gassing. The sealed ampules are sterilized in a steam autoclave (120° C./20 min.).

EXAMPLE 57

An iso-osmotic (isocryoscopic) solution (freezing point depressseion t=—0.156°) is manufactured as follows: 32.25 g. of 4-(2,2-dimethyl-5-phenyl-3-pyrrolidinyl)-pyridine dihydrochloride and 1.768 g. sodium chloride are dissolved in water to 1 liter (pH 2.8–3.1). The resulting solution is filtered fiber-free under nitrogen gassing and filled into 1 cm³-ampules, likewise under nitrogen gassing. The sealed ampules are sterilized in a steam autoclave (120 ° C./20 min.).

We claim:

1. A compound represented by the formula

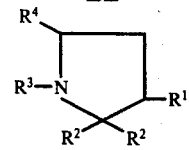

wherein $R^1$ is a pyridyl, $R^2$ is hydrogen or lower alkyl, $R^3$ is hydrogen, lower alkyl or benzyl and $R_4$ is phenyl or phenyl substituted at one or more carbon atoms with one or more of halogen, lower alkyl, lower alkoxy, nitro or amino, and a pharmaceutically acceptable acid addition salt thereof.

2. A compound of claim 1 wherein $R^1$ is 4-pyridyl.
3. A compound of claim 1 wherein $R^2$ is methyl.
4. A compound of claim 1 wherein $R^4$ is phenyl substituted with chlorine or methoxy.
5. A compound of claim 1 wherein $R^1$ is 4-pyridyl, $R^2$ is methyl, $R^3$ is hydrogen, and $R^4$ is phenyl substituted with chlorine or methoxy.
6. A compound of claim 1 which is 4-(2,2-dimethyl-5-phenyl-3-pyrrolidinyl)-pyridine and a pharmaceutically acceptable acid addition salt thereof.
7. A compound of claim 6 which is in the 3R,5S-(cis) form.
8. A compound of claim 1 which is 4-[5-(p-methoxyphenyl)-2,2-dimethyl-3-pyrrolidinyl]-pyridine and a pharmaceutically acceptable acid addition salt thereof.
9. A compound of claim 8 which is in the 3R,5S-(cis) form.
10. An analgesically active composition comprising an analgesically effective amount of a compound of claim 1 and a compatible pharmaceutically acceptable carrier therefor.
11. A compound represented by the formula

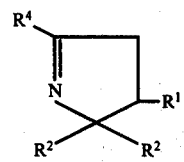

wherein $R^1$ is a pyridyl, $R^2$ is hydrogen or lower alkyl, and $R^4$ is phenyl or phenyl substituted at one or more carbon atoms with one or more of halogen, lower alkyl, lower alkoxy, nitro or amino, an acid addition salt and a N-oxide thereof.

12. A compound according to claim 11 wherein $R^1$ is 4-pyridyl.
13. A compound according to claim 11 wherein $R^2$ is methyl.
14. A compound according to claim 11 wherein $R^1$ is 4-pyridyl, $R^2$ is methyl and $R_4$ is chlorine or methoxy substituted phenyl.
15. A compound of claim 11, 4-(2-phenyl-5,5-dimethyl-1-pyrrolin-4-yl)-pyridine and pharmaceutically acceptable acid addition salts thereof.
16. A compound of claim 11, 4-[2-(p-methoxyphenyl)-5,5-dimethyl-1-pyrrolin-4-yl]-pyridine and pharmaceutically acceptable acid addition salts thereof.

* * * * *